(12) United States Patent
Amorese et al.

(10) Patent No.: US 7,011,949 B2
(45) Date of Patent: Mar. 14, 2006

(54) METHODS AND COMPOSITIONS FOR PRODUCING LABELED PROBE NUCLEIC ACIDS FOR USE IN ARRAY BASED COMPARATIVE GENOMIC HYBRIDIZATION APPLICATIONS

(75) Inventors: Douglas A. Amorese, Los Altos, CA (US); Diane D. Ilsley, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 568 days.

(21) Appl. No.: 10/261,405

(22) Filed: Sep. 30, 2002

(65) Prior Publication Data

US 2004/0063104 A1    Apr. 1, 2004

(51) Int. Cl.
*C12Q 1/68*    (2006.01)
(52) U.S. Cl. .......................................... 435/6
(58) Field of Classification Search ............ None
See application file for complete search history.

(56) References Cited

U.S. PATENT DOCUMENTS

| 5,665,549 A | 9/1997 | Pinkel et al. .................. 435/6 |
| 5,830,645 A | 11/1998 | Pinkel et al. .................. 435/6 |
| 6,197,501 B1 | 3/2001 | Cremer et al. ................. 435/6 |
| 6,335,167 B1 | 1/2002 | Pinkel et al. .................. 435/6 |

*Primary Examiner*—James Martinell (57) ABSTRACT

Methods and compositions for producing labeled probe nucleic acids from genomic nucleic acid template are provided. In the subject methods, a conserved coding consensus region primer is employed to enzymatically generate a select set of labeled probe nucleic acids corresponding to coding regions of genes from a genomic template via a primer extension protocol. The subject methods find use in a variety of different applications, and are particularly suited for use in the preparation of labeled probe nucleic acids for use in array based comparative genomic hybridization applications. Also provided are kits for use in practicing the subject methods.

16 Claims, 2 Drawing Sheets

METHODS AND COMPOSITIONS FOR PRODUCING LABELED PROBE NUCLEIC ACIDS FOR USE IN ARRAY BASED COMPARATIVE GENOMIC HYBRIDIZATION APPLICATIONS

TECHNICAL FIELD

The technical field of this invention is comparative genomic hybridization (CGH)

BACKGROUND OF THE INVENTION

Many genomic and genetic studies are directed to the identification of differences in gene dosage or expression among cell populations for the study and detection of disease. For example, many malignancies involve the gain or loss of DNA sequences resulting in activation of oncogenes or inactivation of tumor suppressor genes. Identification of the genetic events leading to, neoplastic transformation and subsequent progression can facilitate efforts to define the biological basis for disease, improve prognostication of therapeutic response, and permit earlier tumor detection. In addition, perinatal genetic problems frequently result from loss or gain of chromosome segments such as trisomy 21 or the micro deletion syndromes. Thus, methods of prenatal detection of such abnormalities can be helpful in early diagnosis of disease.

Comparative genomic hybridization (CGH) is one approach that has been employed to detect the presence and identify the location of amplified or deleted sequences. CGH reveals increases and decreases irrespective of genome rearrangement. In one implementation of CGH, genomic DNA is isolated from normal reference cells, as well as from test cells (e.g., tumor cells). The two nucleic acids are differentially labeled and then hybridized in situ to metaphase chromosomes of a reference cell. The repetitive sequences in both the reference and test DNAs are either removed or their hybridization capacity is reduced by some means. Chromosomal regions in the test cells which are at increased or decreased copy number can be identified by detecting regions where the ratio of signal from the two DNAs is altered. For example, those regions that have been decreased in copy number in the test cells will show relatively lower signal from the test DNA than the reference compared to other regions of the genome. Regions that have been increased in copy number in the test cells will show relatively higher signal from the test DNA.

In a recent variation of the above traditional CGH approach, the immobilized chromosome element has been replaced with a collection of solid support bound target nucleic acids, e.g., an array of cDNAs. Such approaches offer benefits over immobilized chromosome approaches, but introduce new problems. For example, only a small percentage of the genome is represented in the collection of solid support bound targets and, therefore, only a small percentage of the labeled probe material actually hybridizes to the immobilized targets, which results in low signal intensities for genomic derived probe nucleic acids populations.

Accordingly, there is interest in the development of improved array based CGH protocols.

Relevant Literature

United States Patents of interest include: U.S. Pat. Nos. 6,335,167; 6,197,501; 5,830,645; and 5,665,549.

SUMMARY OF THE INVENTION

Methods and compositions for producing labeled probe nucleic acids from genomic nucleic acid template are provided. In the subject methods, a conserved coding consensus region primer is employed to enzymatically generate a select set of labeled probe nucleic acids corresponding to coding regions of genes from a genomic template via a primer extension protocol. Examples of primers that may be employed in the subject methods include a family of primers containing the 5'-NnATGNn-3' sequence or primers recognizing consensus splice sites such as 5'-ACTTACCTN-3' or 5'-NnAGGNn-3'. The subject methods result in a lower complexity labeled probe population which enables equivalent specific signal to non-specific signal intensities at lower stringency, thus resulting in higher signal and improved signal to background. The subject methods find use in a variety of different applications, and are particularly suited for use in the preparation of labeled probe nucleic acids for use in array based comparative genomic hybridization applications. Also provided are kits for use in practicing the subject methods.

DEFINITIONS

The term "nucleic acid" as used herein means a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

The term "functionalization" as used herein relates to modification of a solid substrate to provide a plurality of functional groups on the substrate surface. By a "functionalized surface" as used herein is meant a substrate surface that has been modified so that a plurality of functional groups are present thereon.

The term "array" encompasses the term "microarray" and refers to an ordered array presented for binding to ligands such as polymers, polynucleotides, peptide nucleic acids and the like.

The terms "reactive site", "reactive functional group" or "reactive group" refer to moieties on a monomer, polymer or substrate surface that may be used as the starting point in a synthetic organic process. This is contrasted to "inert" hydrophilic groups that could also be present on a substrate surface, e.g., hydrophilic sites associated with polyethylene glycol, a polyamide or the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2–50 monomers, preferably about 2–20, more preferably about 3–10 monomers.

The term "ligand" as used herein refers to a moiety that is capable of covalently or otherwise chemically binding a compound of interest. The arrays of solid-supported ligands produced by the methods can be used in screening or separation processes, or the like, to bind a component of interest in a sample. The term "ligand" in the context of the invention may or may not be an "oligomer" as defined above. However, the term "ligand" as used herein may also refer to a compound that is "pre-synthesized" or obtained commercially, and then attached to the substrate.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

An "array," includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays, are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 $\mu$m to 1.0 cm. In other embodiments each feature may have a width in the range of 1.0 $\mu$m to 1.0 mm, usually 5.0 $\mu$m to 500 $\mu$m, and more usually 10 $\mu$m to 200 $\mu$m. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse-jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably. By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only. The term "stringent hybridization conditions" as used herein refers to conditions that are that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 60° C. or higher and 3×SSC (450 mM sodium chloride/45 mM sodium citrate). Another example of stringent hybridization conditions is incubation at 42° C. in a solution containing 30% formamide, 1M NaCl, 0.5% sodium sarcosine, 50 mM MES, pH 6.5. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

DESCRIPTION OF THE SPECIFIC EMBODIMENTS

Methods and compositions for producing labeled probe nucleic acids from genomic nucleic acid template are provided. In the subject methods, a a conserved coding consensus region primer, i.e., a primer recognizing a translation start codon or an exon/intron junction, or set of primers is employed to enzymatically generate labeled probe nucleic acids from a genomic template via a primer extension protocol. The subject methods find use in a variety of different applications, and are particularly suited for use in the preparation of labeled probe nucleic acids for use in array based comparative to genomic hybridization applications. Also provided are kits for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components that are described in the publications which might be used in connection with the presently described invention.

As summarized above the present invention provides methods of producing labeled nucleic acids from genomic template nucleic acid using a conserved primer or set of primers recognizing a translation start codon and/or an exon/intron junction, i.e., a conserved coding consensus region primer, as well as kits for use in practicing the subject methods. In further describing the present invention, the subject methods are discussed first in greater detail, followed by a review of representative kits for use in practicing the subject methods.

Methods

The subject invention provides methods for generating labeled probe nucleic acids from a genomic template, where a feature of the subject methods is the use of a conserved coding consensus sequence primer, usually in the form of a select set of oligonucleotides representing conserved sequences in genes, in a primer extension protocol.

In practicing the subject methods, the first step is to provide a genomic template. By genomic template is meant the nucleic acids that are used as template in the primer extension reactions as described more in the following sections. In many embodiments, the genomic template is a population of genomic deoxyribonucleic acid molecules, where by population is meant a collection of molecules in which at least two constituent members have nucleotide sequences that differ from each other, e.g., by at least about 1 basepair, by at least about 5 basepairs, by at least about 10 basepairs, by at least about 50 base pairs, by at least about 100 base pairs, by at least about 1 kb, by at least about 10 kb etc.

The number of distinct sequences in a population of molecules making up a given genomic template is typically at least 2, usually at least 10 and more usually at least 50, where the number of distinct molecules may be 1000, 5000, 10000, 100000 or higher.

The genomic template may be prepared using any convenient protocol. In many embodiments, the genomic template is prepared by first obtaining a source of genomic DNA, e.g., a nuclear fraction of a cell lysate, where any convenient means for obtaining such a fraction may be employed and numerous protocols for doing so are well known in the art. The genomic template may be genomic DNA representing the entire genome from a particular organism, tissue or cell type or may comprise a portion of the genome, such as a single chromosome. Genomic template may be prepared from a subject, for example a plant or an animal, that is suspected of being homozygous or heterozygous for a deletion or amplification of a genomic region. In many embodiments, the average size of the constituent molecules that make up the genomic template do not exceed about 10 kb in length, typically do not exceed about 8 kb in length and sometimes do not exceed about 5 kb in length, such that the average length of molecules in a given genomic template composition may range from about 1 kb to about 10 kb, usually from about 5 kb to about 8 kb in certain embodiments. The genomic template may be prepared from an initial chromosomal source by fragmenting the source into the genomic template having molecules of the desired size range, where fragmentation may be achieved using any convenient protocol, including but not limited to: mechanical protocols, e.g., sonication, shearing, etc., chemical protocols, e.g., enzyme digestion, etc.

Following preparation of the genomic template, as described above, the prepared genomic template is employed in the preparation of labeled probe nucleic acids in a protocol in which at least one primer, and often a mixture of different primers, typically of greater than 6 nucleotides in length, are employed, where a feature of the employed primers is that they include a sequence of nt residues that is a conserved coding consensus region. By conserved coding consensus region is meant a domain or stretch of nt residues having a sequence of nt residues that hybridizes to (i.e., is the exact complement on (typically under stringent conditions) a translation start codon or an exon/intron junction, e.g., as found in a 5' or 3' splice site. As such, of interest are (N)nATG(N)n containing primers and consensus splice site lo containing primers, wherein each of these types of primers is now described in greater detail below.

The primers employed in the subject methods are typically at least about 6 nt in length. In many embodiments, an oligonucleotide primer employed in the subject methods is one that ranges in length from about 3 to about 25 nt, sometimes from about 5 to about 20 nt and sometimes from about 5 to about 10 nt. By (N)nATG(N)n oligonucleotide primer is meant an oligonucleotide that includes within its length an ATG codon. In other words, random nucleotides, may exist at either the 5' or 3' ends, or both in order to create a primer of greater than 6 nucleotides in length.

In certain embodiments, the primer further includes a 5' domain of random sequence, which random domain may be made up of one or more nucelotide residues, of any base, e.g., degenerate bases, universal bases, modified bases etc. In certain embodiments, the random sequence domain is made up of from about 1 to 10 nt, usually from about 2 to 8 nt, including 3, 4, 5, or 6 nt, etc. In certain embodiments, the random domain is a domain where all possible variations of this random sequence are represented in a primer mix of second primers. For example, in certain embodiments where the spacer is denoted NNNNNN, this representation is intended to indicate that A, G, C, or T can appear at any position, and therefore the spacer six nucleotides of the primers in the set represent all 4096 ($4^6$) possible hexamers.

In certain embodiments, the second strand cDNA primer is described by the formula.

5'-(N)n-ATG(N)n-3' wherein:
ATG are the consecutive nucleotides, A, T and G;
N is any deoxyribonucleotide residue, e.g., A, G, C, T; and
n is 0 or an integer from about 1 to about 10, e.g., from 1 to 8, from 2 to 7, etc, where in many embodiments n is 6.

As summarized above, also of interest are primers that include a consensus splice site. The consensus splice site sequences described by Pertea, M, Lin, X., And Salzber, S. (2001) Nuc. Acids Res. 29, 1185–1190 or similar sequences conserved within the coding portion of a gene can be included in the primer mixture or can be used in place of the (N)nATG(N)n primer, as described above. These primers need not hybridize to the coding strand, but they should extend into the coding portion of the gene (exon) such that they are complimentary to sequences found in double stranded cDNAs. These primers can likewise be extended into non conserved regions by additions of Nn nucleotides to either or both ends. A specific representative primer of this particular embodiment is 5'-ACTTACCTN-3', where N is T or G. Yet another specific representative primer of this particular embodiment is (N)nAgg(N)n (or the complement thereof), where N and n have the meanings ascribed above.

In certain embodiments, the above consensus splice site sequences are from a particular species, e.g., mammal, such as human. Many such splice sites are known to those of skill in the art.

Programs for identifying splice sites in genomic sequences are well known to those of skill in the art, and include, but are not limited to, those described in: (1) Pertea, M, Lin, X., And Salzber, S. (2001) Nuc. Acids Res. 29, 1185–1190; (2) Brunak, et al., "*Prediction of human mRNA donor and acceptor sites from the DNA sequence*" J. Mol. Biol., 220, 49–65, 1991; (3) Reese, M. G. and Eeckman, F. H. (1996) "Splice Sites: A detailed neural network study" Poster at 1996 *Genome Mapping & Sequencing Meeting*, Cold Spring Harbor Laboratory, New York. Splice sites of interest include those that may be identified using any of the above representative or other analogous programs known to those of skill in the art.

In those embodiments where a mixture of primers is employed, a feature of the primer mixture is that it is not a random mixture. As the primer mixture is not a random mixture, at least about 5%, usually at least about 10%, about 20%, about 25%, about 30%, about 40%, about 50% or more of the primers in the mixture are known to include a conserved coding consensus region. In many embodiments, a majority of the primers in the mixture are known to include a conserved coding consensus region, such that more than 50%, e.g., at least about 60%, about 70%, about 80% or more, such as 90%, 95%, 99% or more, including all of, the primers in the mixture are known to include a conserved coding consensus region. As such, in certain embodiments, a known percentage, including a majority, of the primers in the mixture are known to include a sequence that provides for hybridization under stringent conditions to genomic regions in the genomic sample and therefore priming of nucleic acids therefrom.

The primers described above and throughout this specification may be prepared using any suitable method, such as, for example, the known, phosphotriester and phosphite triester methods, or automated embodiments thereof. In one such automated embodiment, dialkyl phosphoramidites are used as starting materials and may be synthesized as described by Beaucage et al. (1981), Tetrahedron Letters 22, 1859. One method for synthesizing oligonucleotides on a modified solid support is described in U.S. Pat. No. 4,458,066. It is also possible to use a primer that has been isolated from a biological source (such as the cleaved products of a restriction endonuclease digest). The primers herein are selected to be "substantially" complementary to each specific sequence to be amplified, i.e.; the primers should be sufficiently complementary to hybridize to their respective targets. Therefore, the primer sequence need not reflect the exact sequence of the target, and can, in fact be "degenerate." Non-complementary bases or longer sequences can be interspersed into the primer, provided that the primer sequence has sufficient complementarity with the sequence of the target to be amplified to permit hybridization and extension.

Figure 2A:
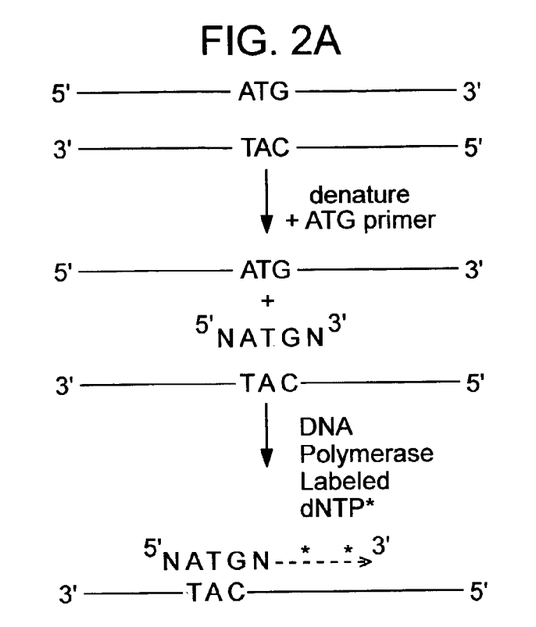
FIGS. 2A and 2B provide schematic representations of the use of different types of primers according to an embodiment of the subject invention.
Figure 2B:
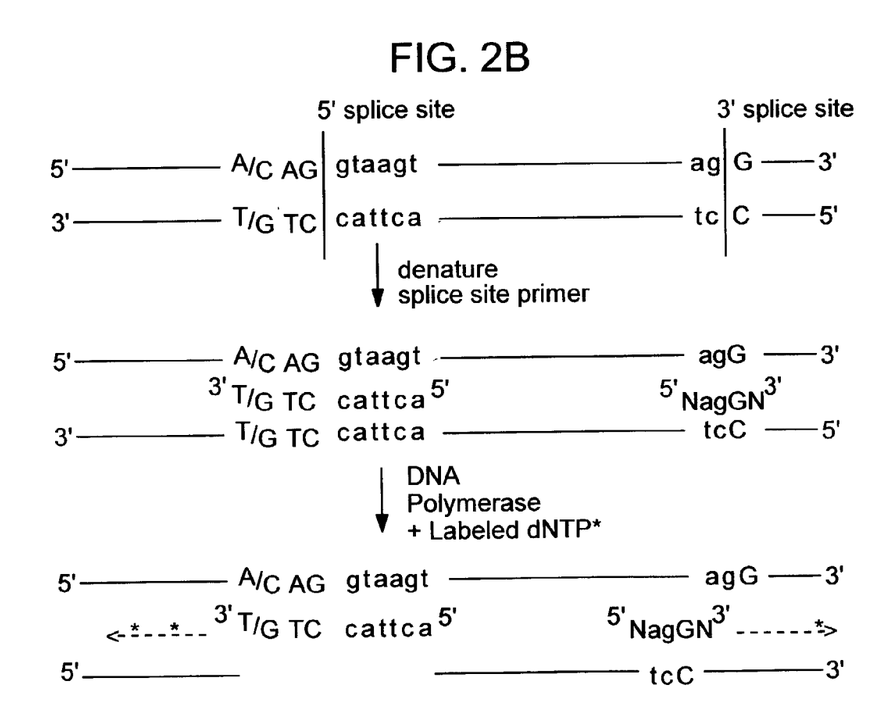

As indicated above, in generating labeled probe nucleic acids according to the subject methods, the above-described genomic template and conserved primer components are employed together in a primer extension reaction that produces the desired labeled probe nucleic acids. Primer extension reactions for generating labeled nucleic acids are well known to those of skill in the art, and any convenient protocol may be employed, so long as the above described genomic template and conserved coding consensus sequence primers are employed. In this step of the subject methods, the primer is contacted with the template under conditions sufficient to extend the primer and produce a primer extension product. As such, the above primers are contacted with the genomic template in the presence of a sufficient DNA polymerase under primer extension conditions sufficient to produce the desired primer extension molecules. DNA polymerases of interest include, but are not limited to, polymerases derived from *E. coli*, thermophilic bacteria, archaebacteria, phage, yeasts, Neurosporas, Drosophilas, primates and rodents, likewise they include polymerases such as Reverse Transcriptases and the like. The DNA polymerase extends the primer according to the genomic template to which it is hybridized in the presence of additional reagents which include, but are not limited to: dNTPs; monovalent and divalent cations, e.g. KCl, $MgCl_2$; sulfhydryl reagents, e.g. dithiothreitol; and buffering agents; e.g. Tris-Cl. This protocol is illustrated in FIGS. 2A and 2B.

As the subject methods are methods of producing labeled probe nucleic acids, extension products that are produced are labeled. In these embodiments, the reagents employed in the subject primer extension reactions typically include a labeling reagent, where the labeling reagent is often a labeled oligonucleotide, which may be labeled with a directly or indirectly detectable label. A directly detectable label is one that can be directly detected without the use of additional reagents, while an indirectly detectable label is one that is detectable by employing one or more additional reagent, e.g., where the label is a member of a signal producing system made up of two or more components. In many embodiments, the label is a directly detectable label, such as a fluorescent label, where the labeling reagent employed in such embodiments is a fluorescently tagged nucleotide(s), e.g. dCTP. Fluorescent moieties which may be used to tag nucleotides for producing labeled probe nucleic acids include, but are not limited to: fluorescein, the cyanine dyes, such as Cy3, Cy5, Alexa 555, Bodipy 630/650, and the like. Other labels may also be employed as are known in the art.

In the primer extension reactions employed in the subject methods of these embodiments, the genomic template is typically first subjected to strand disassociation condition, e.g., subjected to a temperature ranging from about 80° C. to about 100° C., usually from about 90° C. to about 95° C. for a period of time, and the resultant disassociated template molecules are then contacted with the primer molecules under annealing conditions, where the temperature of the template and primer composition is reduced to an annealing temperature of from about 20° C. to about 80° C., usually from about 37° C. to about 65° C. In certain embodiments, a "snap-cooling" protocol is employed, where the temperature is reduced to the annealing temperature, or to about 4° C. or below in a period of from about 1S to about 30S, usually from about 5S to about 10S.

The resultant annealed primer/template hybrids are then maintained in a reaction mixture that includes the above-discussed reagents at a sufficient temperature and for a sufficient period of time to produce the desired labeled probe nucleic acids. Typically, this incubation temperature ranges from about. 20° C. to about 75° C., usually from about 37° C. to about 65° C. The incubation time typically ranges from about 5 min to about 18 hr, usually from about 1 hr to about 12 hr.

The above protocol results in the production of labeled probe nucleic acids. Where desired, the resultant produced labeled probe nucleic acids may be separated from the remainder of the reaction mixture, where any convenient separation protocol may be employed.

Figure 1:
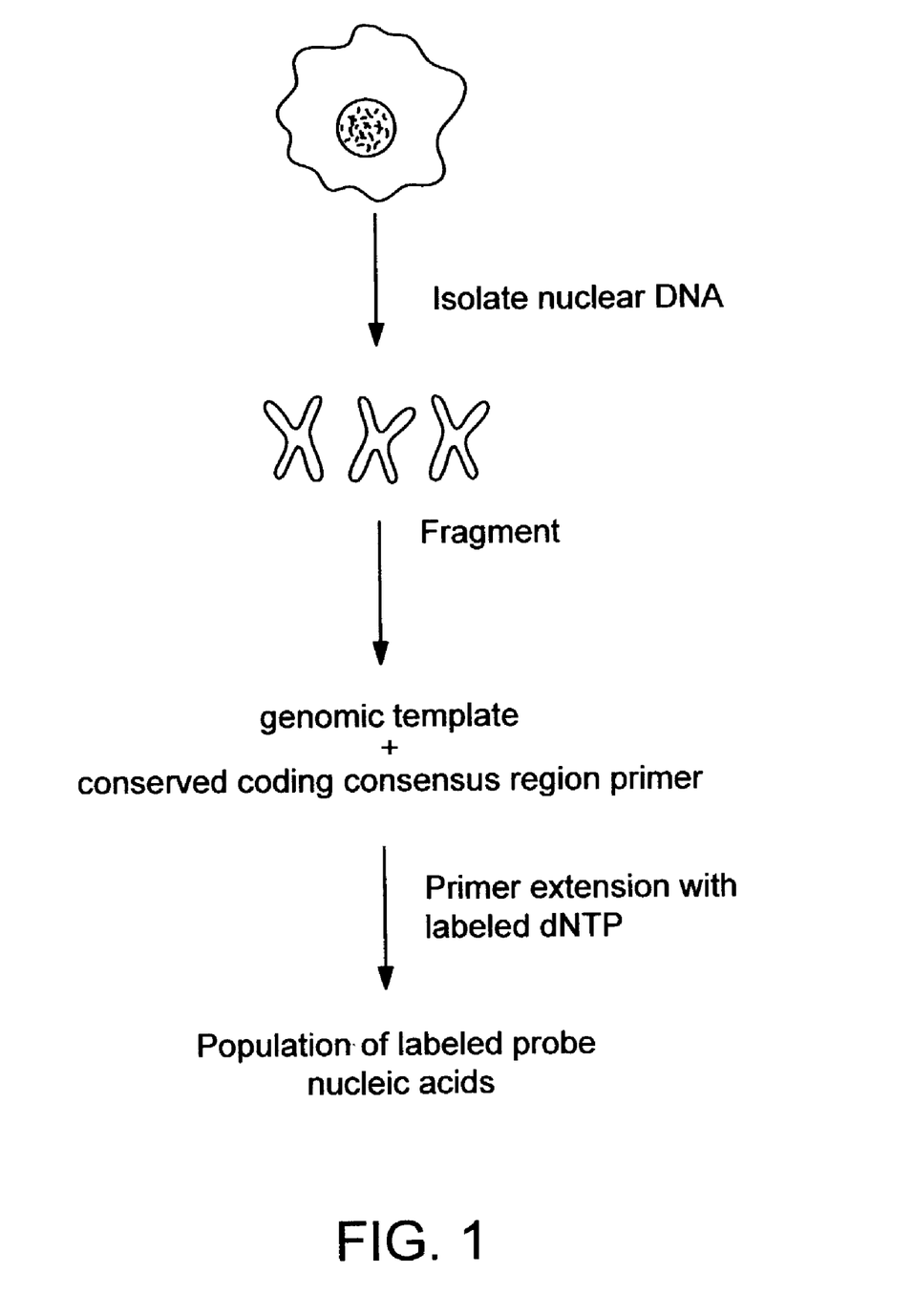
FIG. 1 provides a schematic representation of a method according to the subject invention.

The above protocol results in the production of a select population of labeled probe nucleic acids corresponding to genes and more specifically coding regions within genes from an initial genomic template. A representative protocol is shown in FIG. 1.

Utility

The resultant labeled nucleic acid populations find use in a variety of different applications.

One type of representative application in which the subject methods find use is applications of quantitatively comparing copy number of one nucleic acid sequence in a first collection of nucleic acid molecules relative to the copy number of the same sequence in a second collection. An advantage of the method is that up to 5, sometimes more than 10, usually more than 100 and sometimes more than 1000 copy number comparisons can be made in one hybridization experiment. In these applications, the subject methods are employed to produce at least a first collection of labeled probe nucleic acids and a second collection of labeled probe nucleic acids. In such applications, the first and second labels should be distinguishable from each other. The collections or populations of labeled probe nucleic acids produced by the subject methods are contacted to a plurality of target elements under conditions such that nucleic acid hybridization to the target elements can occur. The probes can be contacted to the target elements either simultaneously or serially, where in many embodiments the probe compositions are contacted with the array of targets simultaneously. As such, the present invention may be used in methods of comparing abnormal nucleic acid copy number and mapping of chromosomal abnormalities associated with disease. In many embodiments, the subject labeling methods are employed in applications that use target nucleic acids immobilized on a solid support, to which differentially labeled probe nucleic acids produced as described above are hybridized.

Hybridization is carried out under suitable hybridization conditions, which may vary in stringency as desired. As such, in certain embodiments highly stringent hybridization conditions may be employed, where in other embodiments low stringency hybridization conditions may be employed. The term "high stringent hybridization conditions" as used herein refers to conditions that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of high stringent hybridization conditions is hybridization at 50° C. or higher and 0.1×SSC (15 mM sodium chloride/1.5 mM sodium citrate). Another example of high stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, followed by washing the filters in 0.1×SSC at about 65° C. High stringent hybridization conditions are hybridization conditions that are at least as stringent as the above representative conditions. Other stringent hybridization conditions are known in the art and may also be employed to identify nucleic acids of this particular embodiment of the invention.

In certain embodiments, hybridization is carried out under low stringency conditions. Representative low stringency conditions include, but are not limited to: (a) hybridization at 5° C. below ½ Tm; (b) hybridization at 50° C. and 6×SSC (0.9 M sodium chloride/0.09 M sodium citrate); (c) or analogous conditions, which can readily be determined by those of skill in the art. The reduced complexity of the probe population enables the binding equilibrium to be shifted in favor of association (lower stringency) in the hybridization reaction without compromising the quality of the result.

The hybridization of the labeled nucleic acids to the target is then detected using standard techniques. Such applications compare the copy numbers of sequences capable of binding to the target elements. Variations in copy number detectable by the methods of the invention may arise in different ways. For example, copy number may be altered as a result of amplification or deletion of a chromosomal region. Alternatively, copy number may be reduced by genetic rearrangements that alter the sequences in the probe or target nucleic acids sufficiently to reduce their binding.

As such, the method may be used for mutation detection, and is most useful for the analysis of multiple gene loci, for example in molecular breeding programs, or in the mapping or identification of genes responsible for polygenic traits.

Target nucleic acids employed in such applications can be derived from virtually any source. Typically, the targets will be nucleic acid molecules derived from representative locations along a chromosome of interest, a chromosomal region of interest, an entire genome of interest, a cDNA library, and the like. These target nucleic acids may be relatively long (typically thousands of bases) fragments of nucleic acid obtained from, for instance, inter-Alu PCR products of genomic clones, restriction digests of genomic clone, cDNA clones and the like. In some embodiments the target nucleic acids are a previously mapped library of clones spanning a particular region of interest.

The choice of target nucleic acids to use may be influenced by prior knowledge of the association of a particular chromosome or chromosomal region with certain disease conditions. International Application WO 93/18186 provides a list of chromosomal abnormalities and associated diseases, which are described in the scientific literature. Alternatively, whole genome screening to identify new region subject to frequent changes in copy number can be performed using the methods of the present invention. In these embodiments, target elements usually contain nucleic acids representative of locations distributed over the entire genome. In some embodiments (e.g., using a large number of target elements of high complexity) all sequences in the genome can be present in the array.

In some embodiments, previously mapped clones from a particular chromosomal region of interest are used as targets. Such clones are becoming available as a result of rapid progress of the worldwide initiative in genomics. Mapped clones can be prepared from libraries constructed from single chromosomes, multiple chromosomes, or from a segment of a chromosome. Standard techniques are used to clone suitably sized fragments in vectors such as cosmids, yeast artificial chromosomes (YACs), bacterial artificial chromosomes (BACs) and P1 phage. While it is possible to generate clone libraries, as described above, libraries spanning entire chromosomes are also available commercially. For instance, chromosome-specific libraries from the human and other genomes are available for Clontech (South San Francisco, Calif.) or from The American Type Culture Collection (see, ATCC/NIH Repository of Catalogue of Human and Mouse DNA Probes and Libraries, 7th ed. 1993). If necessary, clones described above may be genetically or physically mapped. For instance, FISH and digital image analysis can be used to localize cosmids along the desired chromosome. This method is described, for instance, in Lichter et al., Science, 247:64–69 (1990). The physically mapped clones can then be used to more finally map a region of interest identified using CGH or other methods.

The targets employed in the subject methods are immobilized on a solid support. Many methods for immobilizing nucleic acids on a variety of solid surfaces are known in the art. For instance, the solid surface may be a membrane, glass, plastic, or a bead. The desired component may be covalently bound or noncovalently attached through non-specific binding. The immobilization of nucleic acids on solid surfaces is discussed more fully below.

A wide variety of organic and inorganic polymers, as well as other materials, both natural and synthetic, may be employed as the material for the solid surface. Illustrative solid surfaces include nitrocellulose, nylon, glass, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive, materials, cermets or the like. In addition substances that form gels can be used. Such materials include proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. For example, methods for immobilizing nucleic acids by introduction of various functional groups to the molecules is known (see, e.g., Bischoff et al., Anal. Biochem. 164:336–344 (1987); Kremsky et al., Nuc. Acids Res. 15:2891–2910 (1987)). Modified nucleotides can be placed on the target using PCR primers containing the modified nucleotide, or by enzymatic end labeling with modified nucleotides.

Use of membrane supports (e.g., nitrocellulose, nylon, polypropylene) for the nucleic acid arrays of the invention is advantageous in certain embodiments because of well developed technology employing manual and robotic methods of arraying targets at relatively high element densities (e.g., up to 30–40/cm.sup.2). In addition, such membranes are generally available and protocols and equipment for hybridization to membranes is well known. Many membrane materials, however, have considerable fluorescence emission, where fluorescent labels are used to detect hybridization.

To optimize a given assay format one of skill can determine sensitivity of fluorescence detection for different combinations of membrane type, fluorochrome, excitation and emission bands, spot size and the like. In addition, low fluorescence background membranes have been described (see, e.g., Chu et al., Electrophoresis 13:105–114 (1992)).

The sensitivity for detection of spots of various diameters on the candidate membranes can be readily determined by, for example, spotting a dilution series of fluorescently end labeled DNA fragments. These spots are then imaged using conventional fluorescence microscopy. The sensitivity, linearity, and dynamic range achievable from the various combinations of fluorochrome and membranes can thus be determined. Serial dilutions of pairs of fluorochrome in known relative proportions can also be analyzed to determine the accuracy with which fluorescence ratio measurements reflect actual fluorochrome ratios over the dynamic range permitted by the detectors and membrane fluorescence.

Arrays on substrates with much lower fluorescence than membranes, such as glass, quartz, or small beads, can achieve much better sensitivity. For example, elements of various sizes, ranging from the about 1 mm diameter down to about 1 $\mu$m can be used with these materials. Small array members containing small amounts of concentrated target DNA are conveniently used for high complexity comparative hybridizations since the total amount of probe available for binding to each element will be limited. Thus it is advantageous to have small array members that contain a small amount of concentrated target DNA so that the signal that is obtained is highly localized and bright. Such small array members are typically used in arrays with densities greater than $10^4/cm^2$. Relatively simple approaches capable of quantitative fluorescent imaging of 1 $cm^2$ areas have been described that permit acquisition of data from a large number of members in a single image (see, e.g., Wittrup et. al. Cytometry 16:206–213 (1994)).

Covalent attachment of the target nucleic acids to glass or synthetic fused silica can be accomplished according to a number of known techniques. Such substrates provide a very low fluorescence substrate, and a highly efficient hybridization environment.

There are many possible approaches to coupling nucleic acids to glass that employ commercially available reagents. For instance, materials for preparation of silanized glass with a number of functional groups are commercially available or can be prepared using standard techniques. Alternatively, quartz cover slips, which have at least 10-fold lower auto fluorescence than glass, can be silanized.

The targets can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith et al. Science, 258: 1122–1126 (1992)). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

The copy number of particular nucleic acid sequences in two probe collections prepared according to the subject methods are compared by hybridizing the probes to one or more target nucleic acid arrays, as described above. The hybridization signal intensity, and the ratio of intensities, produced by the probes on each of the target elements is determinedSince signal intensities on a target element can be influenced by factors other than the copy number of a probe in solution, it is preferred to conduct an analysis where two labeled populations are present with distinct labels. Thus comparison of the signal intensity ratios among target elements permits comparison of copy number ratios of different sequences in the probe populations.

Standard hybridization techniques are used to probe a target nucleic acid array. Suitable methods are described in references describing CGH techniques (Kallioniemi et al., Science 258:818–821 (1992) and WO 93/18186). Several guides to general techniques are available, e.g., Tijssen, Hybridization with Nucleic Acid Probes, Parts I and II (Elsevier, Amsterdam 1993). For a descriptions of techniques suitable for in situ hybridizations see, Gall et al. Meth. Enzymol., 21:470–480 (1981) and Angerer et al. in Genetic Engineering: Principles and Methods Setlow and Hollaender, Eds. Vol 7, pgs 43–65 (plenum Press, New York 1985). See also U.S. Pat. Nos. 6,335,167; 6,197,501; 5,830,645; and 5,665,549; the disclosures of which are herein incorporate by reference.

Generally, nucleic acid hybridizations comprise the following major steps: (1) immobilization of target nucleic acids; (2) prehybridization treatment to increase accessibility of target DNA, and to reduce nonspecific binding; (3) hybridization of the mixture of nucleic acids to the nucleic acid on the solid surface; (4) posthybridization washes to remove nucleic acid fragments not bound in the hybridization and (5) detection of the hybridized nucleic acid fragments. The reagent used in each of these steps and their conditions for use vary depending on the particular application.

Reading of the resultant hybridized array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER scanner available from Agilent Technologies, Palo Alto, Calif. Other suitable apparatus and methods are described in U.S. patent application Ser. No. 09/846125 "Reading Multi-Featured Arrays" by Dorsel et al.; and Ser. No. 09/430214 "Interrogating Multi-Featured Arrays" by Dorsel et al., which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere).

Results from the reading or evaluating may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample, or whether or not a pattern indicates a particular condition of an organism from which the sample came).

In certain embodiments, the subject methods include a step of transmitting data or results from at least one of the detecting and deriving steps, also referred to herein as evaluating, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

"Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

Analysis of processed results of the described hybridization experiments provides information about the relative copy number of nucleic acid domains, e.g. genes, in genomes.

Kits

Also provided are kits for use in the subject invention, where such kits may comprise containers, each with one or more of the various reagents (typically in concentrated form) utilized in the methods, where such reagents include, but are not limited, the subject conserved primers, buffers, the appropriate nucleotide triphosphates (e.g. dATP, dCTP, dGTP, dTTP), DNA polymerase, labeling reagents, e.g., labeled nucleotides, and the like. Where the kits are specifically designed for use in CGH applications, the kits may further include labeling reagents for making two or more collections of distinguishably labeled nucleic acids according to the subject methods, an array of target nucleic acids, hybridization solution, etc.

Finally, the kits may further include instructions for using the kit components in the subject methods. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

The following examples are offered by way of illustration and not by way of limitation.

Experimental

Genomic DNA from male and female cells isolated using traditional methods (eg Trizol, Qiagen) is restriction digested with 12.5 units of Alu I and Rsa I in the 1× buffer provided by the vendor overnight at 37° C. The digested DNA is purified using the Qiagen PCR Purification kit and concentrated to a final concentration of >0.3 mg/ml in a Speed-Vac.

Two labeling reactions are carried out as described below, the male sample to be ultimately labeled with Cyanine 3, the female with Cyanine 5. A solution containing 6 µg of digested DNA is transferred to a microfuge tube containing 10 µg of conserved primer mix made up of equal amounts of 5'-NNNATG-3' primer and 5'-ACTTACC-3'. The solution is heated to 95° C. for 3–5 minutes and quick cooled by transfer to an ice bath. After 10 minutes on ice reaction components are added to achieve final concentrations below; 50 µM dATP/dTTP/dGTP, 25 µM dCTP, 25 µM labeled dCTP, 1×MMLV reaction buffer and 200 u MMLV-RT. The reaction is transferred to 42 c water bath and allowed to proceed for 60 minutes. Following the reactions the solutions are pooled and the labeled components are purified using the Qiagen PCR Purification kit and concentrated as described previously.

The labeled products are then denatured at 95° C. for 5 minutes, diluted into Agilent's Deposition Hybridization buffer and transferred to an Agilent, Human 1 cDNA microarray. The array is allowed to hybridize overnight at 60° C., washed, scanned and featured extracted according to manufacturers instructions.

Genes present on the X and Y chromosomes are recognized as either having higher Cyanine 3 or Cyanine 5 signals. Genes present on the other chromosomes have a balance of Cyanine 3 and Cyanine 5 signals.

The above results and discussion demonstrate that novel methods of producing labeled probe nucleic acids from genomic template is provided, where advantages of the subject methods include the feature that the produced populations are less complex than genomically produced populations produced by other methods, such as nick translation or random primer extension, and are therefore more suitable for use with immobilized target array based CGH applications. As such, the subject methods represent a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for comparing the relative copy number of nucleic acid sequences in two or more collections of nucleic acid molecules, the method comprising:
   (a) preparing at least a first collection of labeled nucleic acid probe molecules labeled with a first label and a second collection of labeled nucleic acid probe molecules labeled with a second label distinguishable from said first label, wherein each constituent member of said first and second collections of labeled nucleic acid probe molecules is prepared from a genomic nucleic acid template using a set of primers that includes at least one primer comprising a sequence of a conserved coding consensus region;
   (b) contacting said first and second collections of labeled probe molecules with a plurality of target elements bound to a solid surface, each target element comprising a target nucleic acid;
   (c) evaluating the relative binding of the first and second collections of labeled nucleic acid probe molecules to the same target nucleic acid to compare the relative copy number of nucleic acid sequences in said first and second collections of labeled nucleic acid probe molecules.

2. The method according to claim 1, wherein said sequence of a conserved coding consensus region comprises ATG.

3. The method according to claim 2, wherein said ATG comprising primer comprises a sequence of the formula:

$$5'\text{-}(N)n\text{-}ATG\text{-}(N)n\text{-}3',$$

wherein each N is independently any nucleotide residue and each n is independently 0 or an integer from 1 to 10.

4. The method according to claim 1, wherein said sequence of a conserved coding consensus region comprises a consensus splice site.

5. The method according to claim 4, wherein said consensus splice site is a 5' consensus splice site or a 3' consensus splice site.

6. The method of claim 1, wherein the first and second labels are fluorescent labels.

7. The method of claim 1, wherein the solid support is a plurality of beads.

8. The method of claim 1, wherein the solid support is glass.

9. The method of claim 1, wherein said plurality of target elements bound to a solid surface comprise an array.

10. The method of claim 1, wherein the first collection of labeled nucleic acids is from a test genome and the second collection of labeled nucleic acids is from a normal reference genome.

11. The method according to claim 1, wherein said sequence of a conserved coding consensus region is a human sequence.

12. The method according to claim 1, wherein said set of primers is not a random set of primers.

13. The method according to claim 12, wherein at least 5% of said set comprises primers that include a conserved coding consensus region.

14. The method according to claim 1, wherein said contacting step (b) occurs under low stringency conditions.

15. The method according to claim 1, wherein said method further comprises a data transmission step in which a result from said evaluating is transmitted from a first location to a second location.

16. A method comprising receiving data representing a result of said evaluation obtained by the method of claim 1.

* * * * *